United States Patent [19]

Hirotsu et al.

[11] Patent Number: 4,820,418
[45] Date of Patent: Apr. 11, 1989

[54] WATER-ALCOHOL SEPARATING MEMBRANE AND METHOD FOR SEPARATION OF WATER AND ALCOHOL BY THE USE THEREOF

[75] Inventors: Toshihiro Hirotsu, Tsukuba; Shigeru Nakajima, Fuchu, both of Japan

[73] Assignees: Agency of Industrial Science & Technology; Ministry of International Trade & Industry, both of Tokyo, Japan

[21] Appl. No.: 152,039

[22] Filed: Feb. 3, 1988

[30] Foreign Application Priority Data

Feb. 3, 1987 [JP] Japan .................................. 62-22814

[51] Int. Cl.$^4$ ............................................. B01D 13/00
[52] U.S. Cl. .................................. 210/640; 210/500.27
[58] Field of Search ........................... 264/41; 530/353; 210/651, 640, 652, 500.38, 500.27

[56] References Cited

U.S. PATENT DOCUMENTS 4,233,211 11/1980 Ohtomo et al. ...................... 530/353
4,342,711 8/1982 Joh et al. ................................. 264/41

OTHER PUBLICATIONS

Journal of Membrane Science, vol. 23 (1985), pp. 41-58.
Polymer Journal, vol. 17, No. 3 (1985), pp. 499-508.
Journal of Polymer Science, Polymer Letter, vol. 22 (1984), pp. 473-475.
Polymer Journal, vol. 17, No. 2 (1985), pp. 363-368.
Journal of Membrane Science, vol. 24 (1985), pp. 101-119.
Kobunshi Ronbunshu, vol. 42, No. 2 (Feb. 1985), pp. 139-142.
Membrane, 6(3) (19861), pp. 168-184.

*Primary Examiner*—Frank Spear
*Attorney, Agent, or Firm*—Oblon, Fisher, Spivak, McClelland & Maier

[57] ABSTRACT

An insolubilized silk fibroin membrane possesses an ability to permit preferential permeation therethrough of water from a mixture of water and alcohol. When the mixture of water and alcohol is disposed on one side of this membrane and the space on the other side of the membrane is vacuumized, the water from the mixture preferentially permeates through the membrane and the alcohol concentration in the mixture proportionately increases.

4 Claims, 1 Drawing Sheet

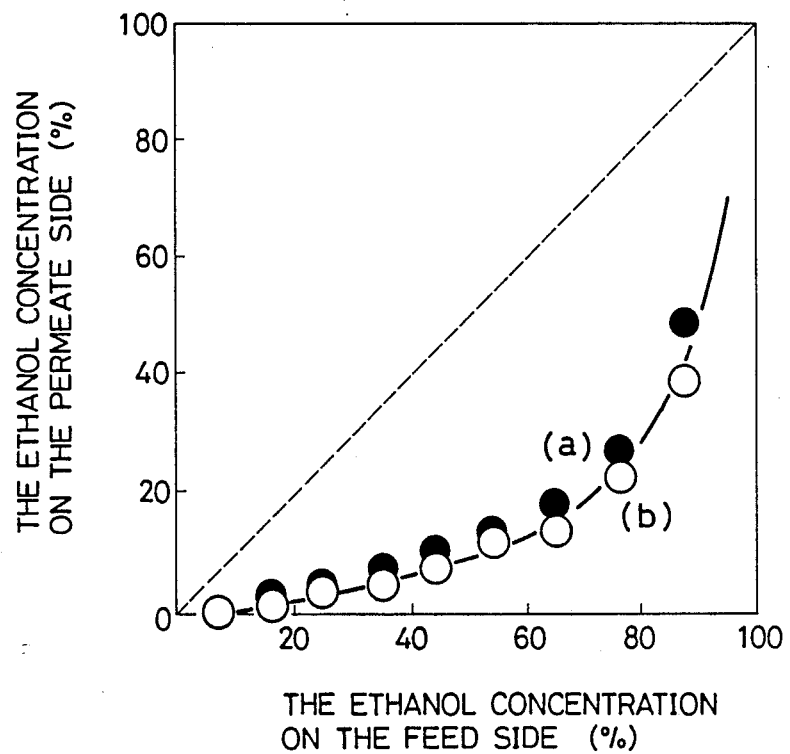

WATER-ALCOHOL SEPARATING MEMBRANE AND METHOD FOR SEPARATION OF WATER AND ALCOHOL BY THE USE THEREOF

BACKGROUND OF THE INVENTION

1. Field of the Invention

This invention relates to a separating membrane formed of silk fibroin, a natural polypeptide, which can be advantageously used for preferential separation of water from a water-alcohol mixture so as to increase the alcohol concentration of the mixture and to a method for increasing alcohol concentration by the use of said membrane.

2. Prior Art Statement

Separation and purification of substances are indispensable operations in numerous fields of the chemical industry. The use of membranes for carrying out these operations is gaining acceptance. Separation processes using dialysis membranes, reverse osmosis membranes, and ultrafiltration membranes have been applied for example, in medical treatment, the desalination of salt water, and the production of extremely pure water. Further, oxygen-permeable membranes and other gas separation membranes are being used in some chemical processes.

While there is known a method for separating an organic substance from an aqueous solution of the organic substance by the selective permeation of the substance through a membrane, this method has not been commercially applied because it is difficult to develop a membrane capable of high-efficiency, high-speed separation. When a membrane capable of efficiently and economically effecting this separation is developed, the aforesaid method will replace such currently used separation processes such as distillation. This will result in a great energy saving and also enable simplification of production.

The separation of substances by a membrane depends on a difference in the ability of the substances to permeate through and diffuse in the membrane. More specifically, the ease with which a substance permeates a membrane increases with increasing ability of the substance for permeation and diffusion in the membrane. Thus, commercial application of the membrane for separation becomes possible when this ability becomes sufficiently high. For the purpose of selective permeation of water, for example, it suffices to form the membrane in a hydrophilic structure.

Various membranes for separating water from a water-alcohol mixture by selective permeation of water in line with the aforesaid principle have been reported. Cellulose acetate membrane [Journal of Membrane Science, Vol. 23, page 41 (1985)], bisphenol-copolymer [Polymer Journal, Vol. 17, page 499 (1985)], acrylic acid-acrylonitrile copolymer membrane [Journal of Polymer Science; Polymer Letter, Vol. 22, page 473 (1983)], N-substituted polyimide-containing copolymer membrane [Polymer Journal, Vol. 17, page 363 (1985) and ibid., Vol. 16, page 653 (1984)], chitosan membrane [Kobunshi Ronbunshu, Vol. 42, page 139 (1985)], and Nafion membrane [Journal of Membrane Science, Vol. 24, page 101 (1985)]. However, none of these membranes are adequate for practical application.

OBJECT AND SUMMARY OF THE INVENTION

An object of the present invention is to provide a novel separating membrane capable of efficiently increasing the alcohol concentration of a water-alcohol mixture by permitting preferential permeation therethrough of the water from the mixture and a method for the concentration of alcohol by the use of the aforementioned separation membrane.

The inventors studied various membranes and found that this object is accomplished by a silk fibroin membrane which is insolubilized and consequently has high affinity for water.

Specifically, this invention is directed to a separating membrane which is obtained by insolubilizing silk fibroin film and consequently made insoluble in a water-alcohol mixture and which is capable of permitting preferential permeation therethrough of the water from the water-alcohol mixture and a method for heightening the alcohol concentration in the water-alcohol mixture by disposing the water-alcohol mixture on one side of the aforementioned separating membrane and vacuumizing the space on the other side of the membrane, thereby causing preferential permeation through the membrane of the water from the water-alcohol mixture.

The silk fibroin membrane is a product obtained by dissolving degummed silk and molding the resultant solution in the form of a membrane.

The above and other objects and features of the invention will become more apparent from the following detailed description with reference to the accompanying drawing.

BRIEF DESCRIPTION OF THE DRAWING

The drawing shows the results of the pervaporation obtained with two fibroin membranes of a fixed thickness of 50 microns, (a) one treated for insolubilization in an aqueous 50% ethanol solution and (b) the other treated in saturated water vapor, as a function of ethanol concentration in the feed and in the permeate.

DETAILED DESCRIPTION OF THE PREFERRED EMBODIMENT

The liquid silk in the silk gland of a silkworm solidifies with simultaneous molecular orientation into a fiber when it is spun out by the silkworm into a cocoon. The silk thread of the cocoon is called raw silk. The raw silk is composed of two fibroin filaments enveloped with sericin. When this raw silk is degummed by being boiled as in soap water, the water-soluble sericin is dissolved out and the fibroin filaments are left behind. The water-alcohol separating membrane of the present invention is a film obtained by molding the silk fibroin in the form of a membrane.

Silk fibroin is a polypeptide formed mainly of glycine and alanine. Though the degummed silk is generally insoluble, it is soluble in a concentrated aqueous solution of lithium bromide. An aqueous solution of pure fibroin can be obtained by dialyzing the solution of fibroin in the aforementioned concentrated aqueous lithium bromide solution thereby removing the lithium bromide. By casting this aqueous solution of pure fibroin on a flat plate and evaporating off the water, there can be obtained a silk fibroin membrane. At this time, the molecular chain of the fibroin assumes a random structure. In this state, the silk fibroin membrane dissolves in water. In this film, a specific interaction continues between the molecular chains of polypeptide. When this film is subjected to a specific treatment, there are formed crystalline peptides of the alpha type and the beta type. As a result, the membrane is rendered insoluble in the water-alcohol mixture. Since the polypeptide is inherently hydrophilic, the membrane consequently obtained exhibits high affinity for water and also excels in mechanical properties such as tensile strength. Thus, this membrane can be used safely and advantageously for the separation of water from a water-alcohol mixture.

There are various methods for insolubilizing the silk fibroin membrane obtained by casting, all of which are known to the art. The insolubilization can, for example, be attained by immersion of the membrane in an organic solvent such as ethanol or exposure thereof to saturated water vapor.

In this invention it does not matter what method is adopted for the insolubilization. Any method can be used so long as it is capable of effecting the insolubilization with high efficiency.

Now, a typical method for efficient preparation of the silk fibroin membrane usable as the water-alcohol separating membrane will be described. First, degummed silk is left immersed overnight in a concentrated aqueous solution of lithium bromide. The concentration of lithium bromide in the aqueous solution is desired to fall in the range of 500 to 2,000 g/liter. Though it is substantially dissolved at the end of the immersion, it is further maintained at 40° C. for about one hour to ensure thorough solution. The resultant solution is passed through a cellophane membrane into distilled water by dialysis for the purpose of removal of lithium bromide. This dialysis is continued until the last sample shows no detectable sign of bromine ion in a test with silver nitrate. The resultant aqueous solution of silver fibroin is cast on an acrylic plate and then air-dried under fixed standard conditions, to give rise to a membrane. The membrane thus obtained is highly soluble in water. This is because the material of membrane assumes a random coil structure as is evident from the infrared spectrum thereof. The produced membrane resembles a transparent cellophane membrane.

This membrane can be insolubilized by immersing it in an aqueous solution of 20 to 100% of ethanol at normal room temperature or exposing it to saturated water vapor. In the infrared absorption spectrum of this membrane, peaks are found at 1,650 cm$^{-1}$ and 1,635 cm$^{-1}$. These peaks are ascribable to the aforementioned alpha and beta type crystalline structures, indicating that the insolubilization has given rise to these crystalline structures. In the course of this insolubilization, there is observed that the strength of the absorption peak due to the beta type crystallization increases in proportion as the ethanol concentration in the water-ethanol mixture under treatment increases. In consequence of the formation of such crystalline structures of fibroin as described above, the membrane undergoes insolubilization and is finally converted into a membrane suitable for water-alcohol separation.

The water-alcohol separation by the use of this membrane is easily effected by the method of pervaporation.

The method of pervaporation effects the separation of a substance from a liquid containing the substance by depositing the liquid in contact with one side of the membrane and vacuumizing the space on the other side of the membrane, thereby creating a difference of concentration on the opposite sides of the membrane ["Maku," Vol. 6, page 168, (1981)]. This method of pervaporation is effective in obtaining separation of an azeotropic mixture or refinement of a mixture of isomers which are not easily separated by distillation.

To realize optimum permeation speed in actual use, the thickness of the separating membrane should be as small as possible and for this it has to have ample strength. Silk fibroin membranes of various thicknesses were used for water-alcohol separation. It was found that the silk fibroin membrane is capable of stable separation of water from a water-alcohol mixture when its thickness is not less than about 10 microns. A membrane of a smaller thickness is difficult to produce because of the inevitable occurrence of pinholes and cracks. To be a fully practicable separating membrane, the silk fibroin membrane has to have a wall thickness of not more than 500 microns.

The fact that this silk fibroin membrane is advantageously useful for water-alcohol separation will be shown below with reference to (a) a sample insolubilized in an aqueous 50% ethanol solution and (b) a sample insolubilized by exposure to saturated water vapor.

The accompanying drawing shows the results of the pervaporation performed on the samples, as a function of the ethanol concentration on the feed side and the permeate side. With either of the samples, the ethanol concentration is notably lower on the permeate side, indicating that the membrane possesses the ability to effect water-alcohol separation by selective permeation therethrough of water.

The separating membrane of the present invention effects the water-alcohol separation by permitting preferential permeation therethrough of water from the water-alcohol mixture. Thus, it can be used for the purpose of increasing the alcohol concentration of a fermentation broth by the removal of water.

Now, the present invention will be described more specifically with reference to working examples.

First, the method of pervaporation used in these examples for the water-alcohol separation will be explained.

First, a circular sample of silk fibroin film 4.7 cm in diameter is set in place in a pressure type stainless steel holder. About 50 ml of a water-alcohol mixture is placed in the holder. The space below the holder, namely, the space on the side of the silk fibroin film opposite to the side contacting the mixture is connected to a vacuum line and vacuumized to the level of about $10^{-1}$ Torr. Then pervaporation starts and is continued for several to about 10 minutes until the permeation reaches a constant rate, at which time the permeate obtained in the space is collected with a liquefied nitrogen trap. The total permeate thus collected over a prescribed period is weighed to determine the permeation rate. Then, the liquids on both sides of the membrane are subjected to gas chromatography and, based on the peak strengths registered on the chromatograms, the water and alcohol concentrations of the liquids are determined.

Now, the method for determining the separation coefficient, $\alpha$, an index of the selectivity of permeation, will be described.

The separation coefficient for water, $\alpha_E^W$, is expressed by the following formula:

$$\alpha_E^W = \frac{Y_W/Y_E}{X_W/X_E}$$

wherein $X_W$ and $X_E$ respectively stand for the concentrations of water and ethanol on the feed side and $Y_W$ and $Y_E$ for those of water and ethanol on the permeate side.

This separation coefficient increases in proportion as the selectivity of permeation is improved.

EXAMPLE 1

An aqueous solution of silk fibroin was obtained by dissolving 2.1 g of degummed silk in an aqueous solution of 9.3 mols of lithium bromide and passing the resultant solution through a cellophane film into distilled water by dialysis, thereby depriving the solution of lithium bromide. The aqueous solution of silk fibroin was cast on an acrylic plate and air-dried to produce a membrane 75 microns in thickness. An insolubilized silk fibroin membrane was produced by keeping the aforementioned membrane immersed in ethanol at room temperature for 2 hours. By the method of pervaporation using this membrane, aqueous solutions containing ethanol in varying concentrations were separated at 40° C. The results are shown below.

| EtOH concentration in feed mixture (%) | Permeation rate (kg/m$^2$ h) | Separation coefficient ($\alpha_E^W$) |
|---|---|---|
| 0.0 | 0.979 | — |
| 8.18 | 0.726 | 18.296 |
| 18.566 | 0.513 | 8.290 |
| 24.829 | 0.416 | 5.249 |
| 34.843 | 0.416 | 5.405 |
| 44.654 | 0.382 | 5.507 |
| 53.901 | 0.311 | 5.780 |
| 67.019 | 0.263 | 7.021 |
| 76.222 | 0.183 | 6.112 |
| 88.452 | 0.177 | 5.036 |

EXAMPLE 2

A cast silk fibroin membrane 75 microns in thickness obtained by following the procedure of Example 1 was exposed to saturated water vapor in a desiccator for 24 hours. As a result, an insolubilized membrane was obtained. The insolubilized membrane was tested for separation by the method of pervaporation at 40° C., with the following results.

| EtOH concentration in feed mixture (%) | Permeation rate (kg/m$^2$ h) | Separation coefficient ($\alpha_E^W$) |
|---|---|---|
| 0.0 | 0.630 | — |
| 8.180 | 0.546 | 29.720 |
| 16.459 | 0.350 | 16.178 |
| 24.829 | 0.318 | 10.261 |
| 34.843 | 0.301 | 21.354 |
| 44.654 | 0.241 | 8.817 |
| 53.901 | 0.198 | 9.861 |
| 67.019 | 0.149 | 11.601 |
| 76.222 | 0.115 | 11.092 |
| 88.452 | 0.068 | 11.101 |

EXAMPLE 3

A cast silk fibroin film 50 microns in thickness was produced by following the procedure of Example 1. It was insolubilized by 2 hours' immersion in an aqueous 50% ethanol solution at room temperature. Water-ethanol separation was tried by the method of pervaporation using this insolubilized membrane. The results obtained at 30° C. were as follows.

| EtOH concentration in feed mixture (%) | Permeation rate (kg/m$^2$ h) | Separation coefficient ($\alpha_E^W$) |
|---|---|---|
| 0.0 | 0.764 | — |
| 16.268 | 0.430 | 8.024 |
| 44.284 | 0.284 | 7.659 |
| 64.753 | 0.193 | 7.410 |

The results of the test at 35° C. were as follows.

| EtOH concentration in feed mixture (%) | Permeation rate (kg/m$^2$ h) | Separation coefficient ($\alpha_E^W$) |
|---|---|---|
| 0.0 | 0.882 | — |
| 16.268 | 0.463 | 8.664 |
| 44.284 | 0.334 | 6.413 |
| 64.753 | 0.251 | 5.799 |

The results obtained at 40° C. were as follows.

| EtOH concentration in feed mixture (%) | Permeation rate (kg/m$^2$ h) | Separation coefficient ($\alpha_E^W$) |
|---|---|---|
| 0.0 | 0.978 | — |
| 16.268 | 0.533 | 7.664 |
| 44.284 | 0.380 | 6.231 |
| 64.753 | 0.273 | 5.872 |

The results obtained at 50° C. were as follows.

| EtOH concentration in feed mixture (%) | Permeation rate (kg/m$^2$ h) | Separation coefficient ($\alpha_E^W$) |
|---|---|---|
| 0.0 | 1.256 | — |
| 16.268 | 0.764 | 10.234 |
| 44.284 | 0.491 | 6.725 |
| 64.753 | 0.352 | 6.288 |

EXAMPLE 4

A cast silk fibroin membrane having the same thickness as that of Example 3 was insolubilized by being treated with saturated water vapor for 24 hours. Water-ethanol separation was tried by the method of pervaporation using the insolubilized membrane at 40° C. The results were as shown below.

| EtOH concentration in feed mixture (%) | Permeation rate (kg/m$^2$ h) | Separation coefficient ($\alpha_E^W$) |
|---|---|---|
| 0.0 | 0.693 | — |
| 7.314 | 0.584 | 11.050 |
| 16.268 | 0.486 | 10.955 |
| 24.755 | 0.427 | 10.235 |
| 34.924 | 0.382 | 10.061 |
| 44.284 | 0.344 | 9.614 |
| 54.174 | 0.287 | 8.621 |
| 64.753 | 0.199 | 11.097 |
| 76.555 | 0.147 | 10.865 |
| 88.054 | 0.111 | 11.713 |

EXAMPLE 5

A cast silk fibroin membrane 20 microns in thickness was insolubilized in 100% ethanol. Water-ethanol separation was tried by the method of pervaporation using the insolubilized membrane at 40° C. The results were as shown below.

| EtOH concentration in feed mixture (%) | Permeation rate (kg/m² h) | Separation coefficient ($\alpha_E^W$) |
| --- | --- | --- |
| 0.0 | 5.664 | — |
| 8.059 | 4.820 | 2.370 |
| 16.491 | 3.711 | 2.760 |
| 25.071 | 3.344 | 2.578 |
| 34.552 | 3.201 | 2.489 |
| 45.226 | 2.940 | 2.834 |
| 54.615 | 2.818 | 3.082 |
| 64.638 | 3.153 | 4.419 |
| 76.735 | 2.996 | 4.374 |
| 88.424 | 3.439 | 3.701 |

EXAMPLE 6

A cast silk fibroin membrane having a thickness of 20 microns was insolubilized with saturated water vapor. Water-ethanol separation was tried by the method of pervaporation using this insolubilized membrane at 40° C. The results were as shown below.

| EtOH concentration in feed mixture (%) | Permeation rate (kg/m² h) | Separation coefficient ($\alpha_E^W$) |
| --- | --- | --- |
| 0.0 | 2.717 | — |
| 8.059 | 2.170 | 8.679 |
| 16.491 | 1.911 | 4.813 |
| 25.071 | 1.635 | 4.030 |
| 34.552 | 1.481 | 4.513 |
| 45.226 | 1.410 | 5.291 |
| 54.615 | 1.672 | 7.258 |
| 64.638 | 1.517 | 8.710 |
| 76.735 | 1.309 | 11.812 |
| 88.424 | 1.303 | 13.964 |

What is claimed is:

1. A method for the separation of water from a water-alcohol mixture, which method comprises subjecting a silk fibroin film to a treatment capable of rendering said silk fibroin film insoluble in said water-alcohol mixture, disposing said water-alcohol mixture on one side of said insolubilized silk fibroin membrane and vacuumizing the space on the other side of said insolubilized silk fibroin membrane, thereby permitting preferential permeation of water from said water-alcohol mixture through said insolubilized silk fibroin membrane and proportionately increasing the alcohol concentration in said water-alcohol mixture.

2. The method according to claim 1, wherein said insolubilization is effected by immersing said silk fibroin film in an organic solvent.

3. The method according to claim 1, wherein said insolubilization is effected by ejxposing said silk fibroin film to water vapor.

4. The method according to claim 1, wherein said membrane has a thickness in the range of 10 to 500 μm.

* * * * *